April 7, 1953 H. C. SWIM Plant Pat. 1,178
ROSE PLANT
Filed April 4, 1952 2 SHEETS--SHEET 1
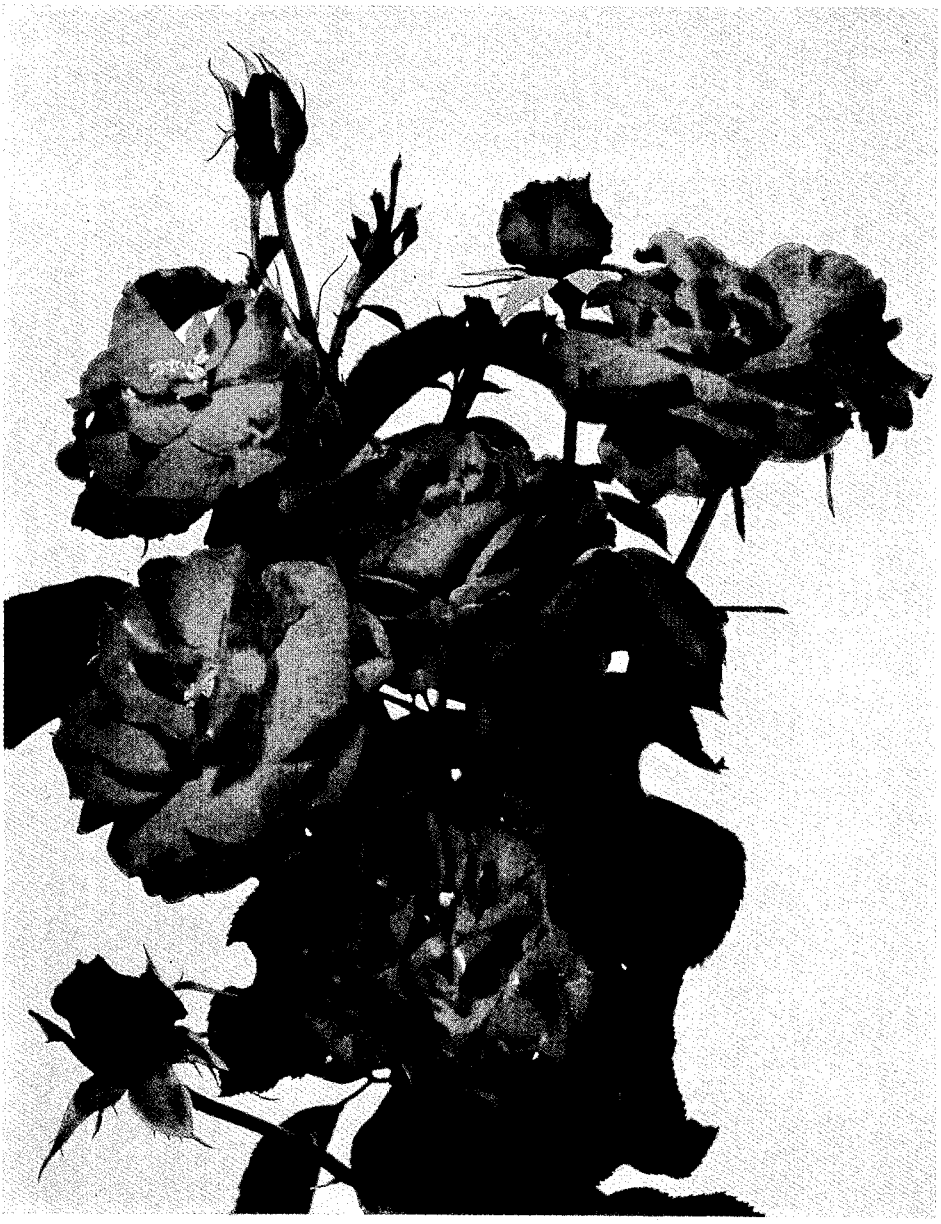
Inventor.
H. C. Swim
By: Robbins & Robb
Attorneys.

ROSE PLANT
Filed April 4, 1952 2 SHEETS—SHEET 2
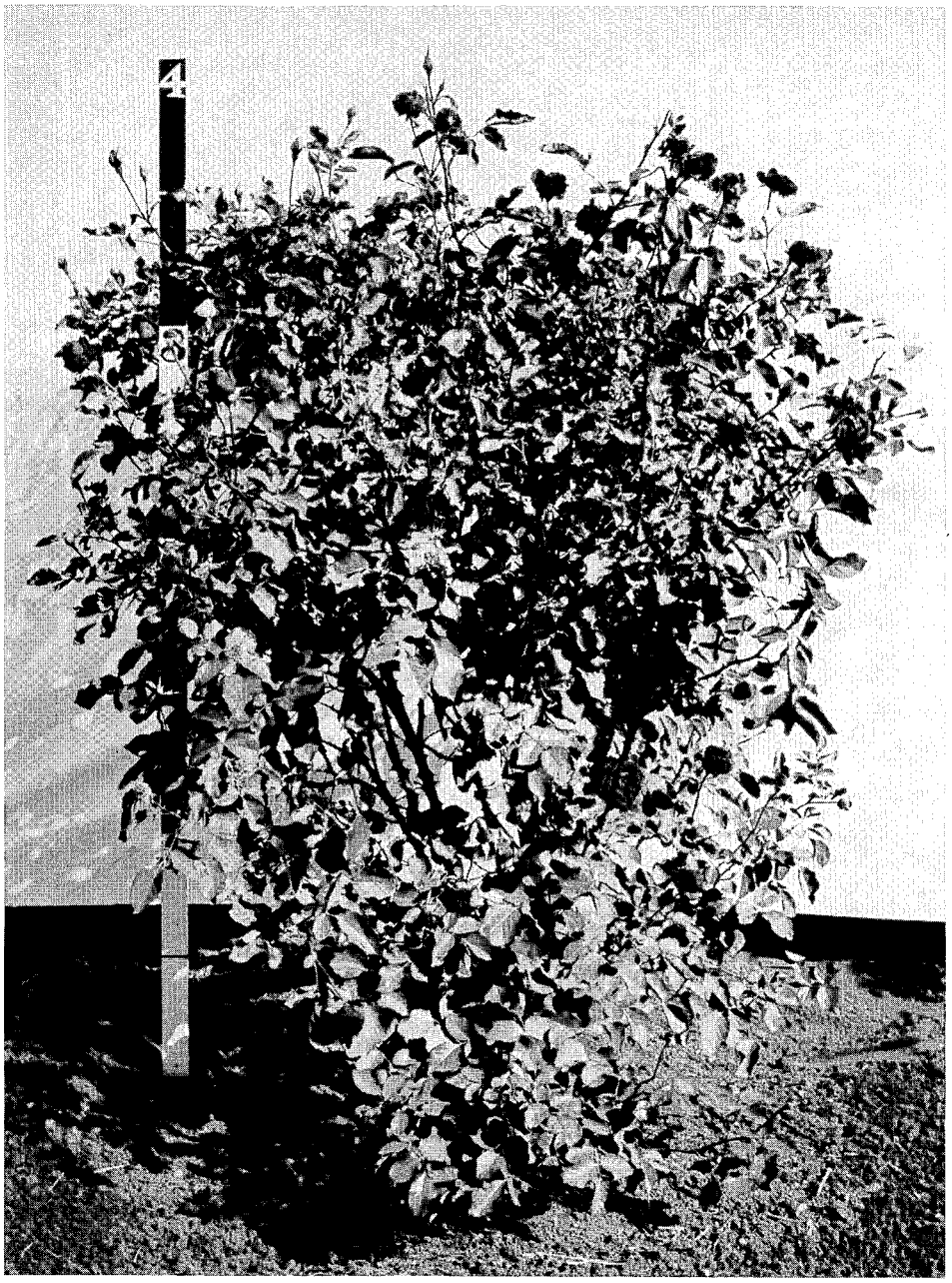
Inventor.
H. C. Swim
By: Robert Cobb
Attorneys Patented Apr. 7, 1953

Plant Pat. 1,178

UNITED STATES PATENT OFFICE 1,178

ROSE PLANT

Herbert C. Swim, Ontario, Calif., assignor to Armstrong Nurseries, Inc., Ontario, Calif., a corporation of California Application April 4, 1952, Serial No. 280,483

1 Claim. (Cl. 47—61)

The present invention relates to a new and distinct variety of rose plant of the hybrid polyantha class, originated by crossing the variety "Minna Kordes," known in the United States as "World's Fair" (Plant Patent No. 362) with the variety "Floradora" (unpatented).

My new variety is distinguished from its parents, as well as from all other varieties of its class, by the following unique combination of outstanding characteristics:

(1) Its very vigorous habit of growth;

(2) The very dark green, large and semi-glossy foilage produced in abundance on a compact bush;

(3) The intensity and brilliance of its red blooms which are produced in abundance and nearly continuously throughout the growing season; and (4) The longer than average peduncle and flowering stem for a rose variety of this type.

In comparison with its seed parent "Minna Kordes," the foliage of my new variety is dark green, semi-glossy and produced in abundance, whereas the foliage of this parent is a lighter green, non-glossy and not as abundant; the blooms as well as the petals of the new variety are smaller in size than those of "Minna Kordes"; the new variety has a much more upright habit of growth and the plants are taller than the more spreading and lower-growing plants of this parent; and my new variety produces more blooms per cluster throughout the growing season than "Minna Kordes."

As compared with the pollen parent "Floradora," the bush of my new variety is more compact but not as upright in its habit of growth as this parent, and the foliage is larger in size; the canes of the new variety are heavier in caliper, with larger prickles on the main stems than in the pollen parent; the blooms of the new variety are a vivid brilliant red, while those of this parent are a much lighter shade of red, approaching orange; and the hips produced by the new variety are larger than those produced by the parent.

Asexual reproduction of my new variety by budding at Ontario, California, shows that the foregoing characteristics and distinctions come true to form and are established and transmitted through succeeding propagations.

The accompanying drawings show in color specimen flowers and foliage of my new variety in different stages of development, and also show in black-and-white a typical plant of the new variety which is illustrative of its vigorous and upright habit of growth as indicated by the marker beside the plant, graduated in feet, and also illustrative of the typical abundance of foliage on the compact bush.

The following is a detailed description of the new variety, with color terminology in accordance with Robert F. Wilson's Horticultural Colour Chart, except where Ridgway's Color Standards and Nomenclature are indicated, or where general color terms of ordinary dictionary significance are obvious:

Type: Bush; outdoor; seedling; for cut flowers and for garden decoration.

Class: Hybrid polyantha.

Breeding: Seedling.

*Seed parent.*—"Minna Kordes" ("World's Fair" in U. S.)

*Pollen parent.*—"Floradora."

Propagation: Holds its distinguishing characteristics through succeeding propagations by budding.

*Flower*

Locality where grown and observed: Ontario, California.

Flowers borne: Usually 4 to 5 or more to stem; in regular, somewhat rounded cluster, on strong, medium to long stems.

Quantity of bloom: Abundant, outdoors.

Continuity: Nearly continuous during growing season.

Fragrance: Moderate to strong; spicy.

Bud:

*Peduncle.*—Long; average caliper to heavy; erect; smooth; some gland-tipped cilia and few prickles. Color—near Kildare green, Plate XXXI (Ridgway) and Absinthe Green, Plate XXXI (Ridgway), shaded with Deep Corinthian Red, Plate XXVII (Ridgway) and Indian Red, Plate XXVII (Ridgway).

*Before calyx breaks.*—Size—medium. Form—Medium length; ovoid; with foliaceous appendages, tomentum, and gland-tipped cilia on the surface of the bud; usually without bristle-like foliaceous parts extending beyond the tip of the bud.

*As calyx breaks.*—Color—between Cardinal Red, Plate 822, page 168 and Chrysanthemum Crimson, Plate 824, page 169.

*Sepals.*—Inner surface—with fine, woolly tomentum; margins variable; sometimes with appendages and stipitate glands; sometimes lined with woolly tomentum.

*As first petal opens.*—Size—average. Form ovoid. Color: outside—between Cardinal Red, Plate 822, page 168, and Chrysanthemum Crimson, Plate 824, page 169; small area at base near Carmine, Plate 21/3, page 21, shading into near Aureolin, Plate 3/3, page 3; inside—near Blood Red, Plate 820, page 166, shading to near Currant Red, Plate 821, page 167, toward margin; small area at base near Carmine, Plate 21/3, page 21, shading into near Aureolin, Plate 3/3, page 3.

*Opening.*—Opens up well; is not retarded from opening by cold, hot, wet or dry weather.

Bloom:

*Size, when fully open.*—Average; 2½ inches to 3 inches.

*Petalage.*—Semi-double; from 19 to 25 petals, plus 4 to 7 petaloids; arranged regularly.

*Form.*—High-centered at first; becoming open to somewhat cupped or saucer-shaped; petals being at first loosely cupped, with tips slightly reflexed; becoming later, at maturity, flat-cupped, with tips sometimes somewhat rolled inward.

Petals:

*Texture.*—Medium to thick; leathery; with inside velvety and outside satiny.

*Shape.*—Outside — broadly obovate, with apex flat; sometimes with 1 or 2 notches. Intermediate—broadly obovate, with apex rounded; sometimes with 1 or 2 notches. Inside—obovate; somewhat irregular, with apex rounded; sometimes with 1 or 2 notches.

This description of a newly opened flower was made from a rose grown outdoors in the month of August, at Ontario, California:

*Color.*—Outside petal: outside surface—near Cardinal Red, Plate 822/1, page 168; small area at base near attachment near Carmine, Plate 21/3, page 21, shading into near Aureolin, Plate 3/3, page 3; inside surface—between Orient Red, Plate 819, page 165, and Blood Red, Plate 820, page 166, shading to near Currant Red, Plate 821, page 167, toward margins; small area at base near attachment near Carmine, Plate 21/3, page 21, shading into near Aureolin, Plate 3/3, page 3. Intermediate petal: outside surface—near Cardinal Red, Plate 822/1, page 168; small area at base near attachment near Carmine, Plate 21/3, page 21, shading into near Aureolin, Plate 3/3, page 3; inside surface—between Orient Red, Plate 819, page 165, and Blood Red, Plate 820, page 166, shading to near Currant Red, Plate 821, page 167, toward margins; small area at base near attachment near Carmine, Plate 21/3, page 21, shading into near Aureolin, Plate 3/3, page 3. Inner petal: outside surface—near Cardinal Red, Plate 822/1, page 168; small area at base near attachment near Carmine, Plate 21/3, page 21, shading into near Aureolin, Plate 3/3, page 3; inside surface—between Orient Red, Plate 819, page 165, and Blood Red, Plate 820, page 166, shading to near Currant Red, Plate 821, page 167, toward margins; small area at base near attachment near Carmine, Plate 21/3, page 21, shading into near Aureolin, Plate 3/3, page 3.

This description was made from a rose that was open for three days outdoors in the month of September, at Ontario, California:

*Color.*—Outside petal: outside surface—near Currant Red, Plate 821/2, page 167; small area at base near Carmine, Plate 21/3, page 21, shading into near Aureolin, Plate 3/3, page 3; inside surface—between Orient Red, Plate 819/2, page 165, and Blood Red, Plate 820/2, page 166; small area at base near Carmine, Plate 21/3, page 21, shading into Aureolin, Plate 3/3, page 3. Inside petal: outside surface—near Currant Red, Plate 821/2, page 167; small area at base near Carmine, Plate 21/3, page 21, shading into near Aureolin, Plate 3/3, page 3; inside surface—between Orient Red, Plate 819/2, page 165, and Blood Red, Plate 820/2, page 166; small area at base near Carmine, Plate 21/3, page 21, shading into Aureolin, Plate 3/3, page 3.

*General color effect.*—Newly opened flower—between Orient Red, Plate 819, page 165, and Blood Red, Plate 820, page 166. Three days open—between Orient Red, Plate 819/2, page 165, and Blood Red, Plate 820/2, page 166.

*Behavior.*—Drop off cleanly; petals tend to persist more in cold weather; petals also tend to blue in cold weather with black markings occurring, particularly, near margins of petals of the older blooms; not affected too greatly by hot weather.

*Flower longevity.*—On bush in garden—4 to 5 days in September. Cut roses grown outdoors kept at living-room temperatures—5 days in September.

*Reproductive organs*

Stamens: Average number; arranged regularly about pistils, with a few mixed with petaloids.

Filaments: Short; 3 to 5 mm. long; most with anthers. Color—near Crimson, Plate 22/2, page 22.

Anthers: Medium size; all open at once approximately. Color: upper side—margin near Indian Yellow, Plate 6/1, page 6; remainder near Carmine, Plate 21/3, page 21; under side—margin near Indian Yellow, Plate 6/1, page 6; remainder near Carmine, Plate 21/3, page 21.

Pollen: Moderate. Color—near Saffron Yellow, Plate 7/1, page 7.

Pistils: Average number; approximately 50 in number.

Styles: Even; average length; average caliper; 10 to 12 mm. long; bunched. Color—near Geranium Lake, Plate 20/1, page 20.

Stigma: Color—Canary Yellow, Plate 2/3, page 2, to Aureolin, Plate 3/3, page 3.

Ovaries: Most enclosed in, some protruding from, calyx.

Hips: Average length; globular; smooth; walls thick, fleshy. Color (¾ mature)—between Lettuce Green, Plate V (Ridgway), and Parrot Green, Plate VI (Ridgway).

Sepals: Usually falling soon; medium length; mostly spear-shaped. Color: inside — near Light Cress Green, Plate XXXI (Ridgway); usually shaded with Indian Red, Plate XXVII (Ridgway), to Dark Indian Red, Plate XXVII (Ridgway); outside—near Absinthe Green, Plate XXXI (Ridgway); usually shaded with Indian Red, Plate XXVII (Ridgway), to Dark Indian Red, Plate XXVII (Ridgway).

Seeds: Few to average number; medium size; 5 to 11 in number.

*Plant*

Foliage:

*Leaves.*—Compound of usually 5 to 7 leaflets; abundant; large; leathery and semi-glossy.

*Leaflets.*—Shape—broadly obovoid, with apex acute. Base—round. Margin—doubly serrate.

*Color.*—Mature: upper surface—between Dark Dull Yellow-Green, Plate XXXII (Ridgway), and Empire Green, Plate XXXII (Ridgway); under surface—near Chromium Green, Plate XXXII (Ridgway). Young: upper surface—near Cress Green, Plate XXXI (Ridgway), shaded with near Dark Mineral Red, Plate XXVII (Ridgway); under surface—near Mineral Red, Plate XXVII (Ridgway).

*Rachis.*—Average size to heavy. Upper side—grooved, with some stipitate glands on edges. Under side—sparsely prickly and with stipitate glands.

*Stipules.*—Medium length to long; moderately wide, with medium length points turning out at an angle of less than 45°.

*Disease.*—Average resistance to mildew when compared with other varieties of hybrid polyantha under comparable field or garden conditions.

Growth:

*Habit.*—Upright-spreading; much-branched.

*Growth.*—Very vigorous.

*Canes.*—Heavy.

*Main stems.*—Color—between Parrot Green, Plate VI (Ridgway), and Cedar Green, Plate VI (Ridgway). Large prickles—several to many; medium length; hooked slightly downward; with medium length, narrow base; color—Cinnamon, Plate XXIX (Ridgway), to Mikado Brown, Plate XXIX (Ridgway). Small prickles—none. Hairs—none.

*Branches.*—Color—near Parrot Green, Plate VI (Ridgway). Large prickles—several; medium length; hooked slightly downward; with medium length, narrow base; color—between Chamois, Plate XXX (Ridgway) and Honey Yellow, Plate XXX (Ridgway). Small prickles—few; color—between Chamois, Plate XXX (Ridgway) and Honey Yellow, Plate XXX (Ridgway). Hairs—none.

*New shoots.*—Color—near Absinthe Green, Plate XXXI (Ridgway), shaded with Deep Corinthian Red, Plate XXVII (Ridgway) to Ocher Red, Plate XXVII (Ridgway). Large prickles—several; medium length; hooked slightly downward; with narrow base; color—near Mineral Red, Plate XXVII (Ridgway). Small prickles—few; color—near Mineral Red, Plate XXVII (Ridgway). Hairs—none.

I claim:

A new and distinct variety of rose plant, substantally as herein shown and described, characterized as to novelty particularly by its very vigorous habit of growth, by the very dark green, large and semi-glossy foliage produced in abundance on a compact bush, by the intensity and brilliance of the red color of its blooms, by the abundance and substantially continuous production of its blooms throughout the growing season, and by its longer than average peduncle and flowering stem for a variety of this type.

HERBERT C. SWIM.

No references cited.